US006271372B1

(12) United States Patent
Roduit et al.

(10) Patent No.: US 6,271,372 B1
(45) Date of Patent: *Aug. 7, 2001

(54) PROCESS FOR THE PREPARATION OF ARYLAMIDES OF HETEROAROMATIC CARBOXYLIC ACIDS

(75) Inventors: Jean-Paul Roduit, Grône; Georges Kalbermatten, Ausserberg, both of (CH)

(73) Assignee: Lonza AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/239,551

(22) Filed: Jan. 29, 1999

Related U.S. Application Data

(60) Division of application No. 08/926,455, filed on Sep. 10, 1997, now Pat. No. 5,900,484, which is a continuation-in-part of application No. 08/850,393, filed on May 2, 1997, now Pat. No. 5,892,032.

(30) Foreign Application Priority Data

May 9, 1996 (CH) .................................................. 1178/96
Sep. 18, 1996 (CH) .................................................. 2279/96

(51) Int. Cl.⁷ .................................................. C07D 251/30
(52) U.S. Cl. ........................ 544/215; 544/182; 544/319; 544/406; 544/407; 544/335; 546/323; 546/317; 546/276.1
(58) Field of Search .................................. 546/323, 317; 544/182, 319, 406, 407, 215, 335

(56) References Cited

U.S. PATENT DOCUMENTS

| 4,128,554 | 12/1978 | Heck ................................. 546/317 |
| 4,254,125 | 3/1981 | Sunder et al. .................... 544/408 |
| 4,618,366 | 10/1986 | Cramp et al. ..................... 546/291 |
| 5,159,113 | 10/1992 | Nicholas ............................ 564/132 |
| 5,294,597 | 3/1994 | Foster et al. ...................... 504/255 |
| 5,380,861 | 1/1995 | Scalone et al. .................... 546/323 |
| 5,534,635 | 7/1996 | Scalone et al. .................... 546/323 |
| 5,759,956 | 6/1998 | Niedermann et al. ............. 504/255 |

FOREIGN PATENT DOCUMENTS

| 0053011 | 6/1982 | (EP) . |
| 0447004 | 9/1991 | (EP) . |
| 0582825 | 2/1994 | (EP) . |
| WO 94/27974 | 12/1994 | (WO) . |

OTHER PUBLICATIONS

Ben–David et al., Journal of the American Chemical Society, vol. 111, No. 23, (1989), pp 8742–8744 J. Heterocycl. Chem., (1990), 27, 243.

Primary Examiner—Jane Fan
(74) Attorney, Agent, or Firm—Fisher, Christen & Sabol

(57) ABSTRACT

A process for the preparation of arylamides of heteroaromatic carboxylic acids of the formula:

I

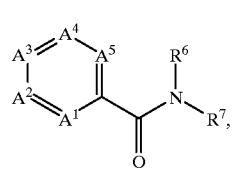

in which each $A^n$ is nitrogen or $CR^n$ (n=1 to 5), with the proviso that at least one of the ring members is nitrogen and that two nitrogen atoms are not bonded directly to one another; $R^1$ to $R^5$, if present, independently of one another are hydrogen, $C_{1-4}$-alkyl or aryl, one of the substituents $R^1$ to $R^5$ being a group of the formula —OR, in which R is an optionally substituted aromatic or heteroaromatic radical; $R^6$ is hydrogen or $C_{1-4}$-alkyl; and $R^7$ is an optionally substituted aromatic or heteroaromatic radical. The amides are obtained from the corresponding heteroaromatic halogen compounds, the corresponding aromatic amines and carbon monoxide in the presence of a palladium phosphine complex. Compounds of this class are important herbicides.

27 Claims, No Drawings ic acids by reacting
PROCESS FOR THE PREPARATION OF ARYLAMIDES OF HETEROAROMATIC CARBOXYLIC ACIDS This application is a division of 08/926,455, Sep. 10, 1997 now U.S. Pat. No. 5,900,484 which is a continuation-in-part of U.S. Ser. No. 08/850,393, filed on May 2, 1997 now U.S. Pat. No. 5,892,032.

BACKGROUND OF THE INVENTION

1. Field of the Invention

The invention relates to a process for the preparation of arylamides of heteroaromatic carboxylic acids by reacting heteroaromatic halogen compounds with carbon monoxide and aromatic amines in the presence of a catalyst and a base. The invention further relates to a novel halogenopyridine as a starting material for the preparation, according to the invention, of an arylamide.

The amides which can be prepared according to the invention have the general formula:

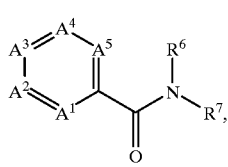

in which:
$A^1$ is nitrogen or $CR^1$,
$A^2$ is nitrogen or $CR^2$,
$A^3$ is nitrogen or $CR^3$,
$A^4$ is nitrogen or $CR^4$ and
$A^5$ is nitrogen or $CR^5$,
with the proviso that at least one of the ring members $A^1$ to $A^5$ is nitrogen and that two nitrogen atoms are not bonded directly to one another;
$R^1$ to $R^5$, if present, independently of one another are hydrogen, $C_{1-4}$-alkyl or aryl, but one of the substituents $R^1$ to $R^5$ is a group of the formula —OR, in which R is an optionally substituted aromatic or heteroaromatic radical;
$R^6$ is hydrogen or $C_1$4-alkyl; and
$R^7$ is an optionally substituted aromatic or heteroaromatic radical.

Said amides include especially the arylamides of pyridine-, pyrimidine-, pyrazine- and 1,3,5-triazinecarboxylic acids.

2. Background Art

Numerous compounds of the structure of formula I, especially those in which one of the substituents $R^1$ to $R^5$ is an aryloxy group (—OR) adjacent to a ring nitrogen atom, are important herbicides (International Published Patent Application No. 94/27974, European Published Patent Application No. 0,053,011 and European Published Patent Application No. 0,447,004). The synthesis of these known compounds is conventionally based on the corresponding carboxylic acids or carboxylic acid derivatives (acid chlorides, esters, nitrites), although these are often difficult to obtain and therefore expensive.

BROAD DESCRIPTION OF THE INVENTION

The main object of the invention was to provide an alternative process based on more easily obtainable educts. Other objects and advantages of the invention are set out herein or are obvious herefrom to one skilled in the art.

The objects and advantages of the invention are achieved by the processes and compound of the invention.

It has been found that halogen compounds of the general formula:

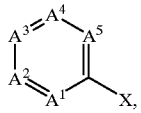

in which $A^1$ to $A^5$ are as defined above and X is chlorine, bromine or iodine, react directly with carbon monoxide and a primary or secondary amine of the general formula:

$$R^6\text{—NH—}R^7 \qquad \text{III,}$$

in which $R^6$ and $R^7$ are as defined above, in the presence of a base, to give a good to almost quantitative yield of the desired products (I) when a complex of palladium with a triphenylphosphine of the general formula:

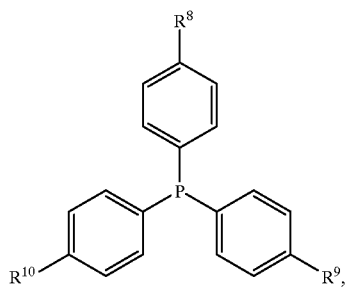

in which $R^8$ to $R^{10}$ independently of one another are $C_{1-4}$-alkyl, $C_{1-4}$-alkoxy, benzyloxy or fluorine, is present as a catalyst.

The presence of the substituents $R^8$ to $R^{10}$ in the 4-position (para position) of the phenyl groups has proved to be an essential feature here. The corresponding ortho-substituted and meta-substituted compounds, like the unsubstituted triphenylphosphine, give considerably poorer yields or no product at all.

DETAILED DESCRIPTION OF THE INVENTION

Herein, $C_{1-4}$-alkyl is to be understood as meaning any linear or branched primary, secondary or tertiary alkyl groups having up to 4 carbon atoms. Herein, aromatic or heteroaromatic radicals are to be understood as meaning especially monocyclic or polycyclic systems, such as, phenyl, naphthyl, biphenylyl, anthracenyl, furyl, pyrrolyl, pyrazolyl, thiophenyl, pyridyl, indolyl or quinolinyl. These can carry one or more identical or different substituents, for example, lower alkyl groups such as methyl, halogenated alkyl groups such as trifluoromethyl, lower alkoxy groups such as methoxy, or lower alkylthio (alkanesulfanyl) or alkanesulfonyl groups such as methylthio or ethanesulfonyl. Substituted phenyl is to be understood as meaning especially groups such as fluorophenyl, methoxyphenyl, tolyl or trifluoromethyl, wherein the substituents are preferably in the para position.

The halogen compounds (II) used as starting materials are either known compounds or can be prepared analogously to known compounds. Numerous compounds of this type are published, for example, in U.S. Pat. No. 4,254,125 and European Published Patent Application No. 0,001,187. The compound 2-chloro-6-[1-methyl-3-(trifluoromethyl) pyrazol-5-yloxy]pyridine is novel and also forms a subject of the present invention.

The process according to the invention is preferentially suitable for the preparation of amides (I) in which $A^2$ is nitrogen and forms a pyridine ring with the remaining ring members.

Particularly preferred amides (I) are those in which $R^1$ is a group of the formula —OR, R being as defined above.

Other preferred amides (I) are those in which $A^1$ is nitrogen and forms a pyridine ring with the remaining ring members,
those in which $A^1$ and $A^5$ are nitrogen and form a pyrimidine ring with the remaining ring members,
those in which $A^1$ and $A^4$ are nitrogen and form a pyrazine ring with the remaining ring members,
and those in which $A^1$, $A^3$ and $A^5$ are nitrogen and form a 1,3,5-triazine ring with the remaining ring members.

In the last four classes mentioned, particularly preferred amides are those in which $R^2$ is a group of the formula —OR, R being as defined above.

Other preferred amides (I) are those in which R is an optionally substituted phenyl group. This applies especially to the above mentioned amides with a pyridine, pyrimidine, pyrazine or 1,3,5-triazine ring in which $R^1$ or $R^2$ is a group of the formula —OR.

Other preferred amides are those in which $R^6$ is hydrogen and $R^7$ is an optionally substituted phenyl group.

Preferred halogen compounds (II) are the chlorine compounds (X is Cl).

Particularly preferred triphenylphosphines (IV) are those in which $R^8$ to $R^{10}$ are identical and are $C_{1-4}$-alkoxy or benzyloxy groups.

The triphenylphosphine in which $R^8$ to $R^{10}$ are methoxy groups is very particularly preferred.

The catalytically active palladium phosphine complex is advantageously formed in situ by a process in which palladium in finely divided elemental form (e.g., palladium on activated charcoal), a Pd(II) salt (e.g., the chloride or the acetate) or a suitable Pd(II) complex [e.g., dichlorobis (triphenylphosphine)palladium(II)] is reacted with the phosphine. The particularly preferred palladium source is palladium(II) acetate. The palladium is preferably used in an amount of 0.02 to 0.2 mol percent of Pd(II) or 0.5 to 2 mol percent of Pd(0) (as Pd/C), based in each case on the halogen compound (II). The phosphine is advantageously used in excess (based on Pd), preferably in an amount of 0.2 to 5 mol percent, again based on the halogen compound (II).

The solvents used can be either relatively non-polar, for example, methylcyclohexane, toluene or xylene, or polar, for example, acetonitrile, tetrahydrofuran, pyridine, butyl acetate, N-methylpyrrolidone, methyl isobutyl ketone or N,N-dimethylacetamide. Particularly good results have been achieved with non-polar solvents, especially with methylcyclohexane or xylene.

The base used is preferably a relatively weak base. This does not need to be soluble in the solvent used. Examples of suitable bases are carbonates such as sodium or potassium carbonate, (hydrogen-) phosphates such as tripotassium phosphate, dipotassium hydrogen phosphate or disodium hydrogen phosphate, or acetates such as sodium acetate. Particularly good results have been achieved with sodium carbonate or dipotassium hydrogen phosphate.

The reaction temperature is preferably 800 to 250° C.

The carbon monoxide pressure is preferably 1 to 50 bar.

The halogen compounds (II) are advantageously prepared by reacting a dihalide of the general formula:

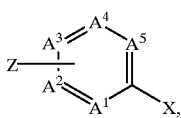

V in which X is chlorine, bromine or iodine and $A^1$ to $A^5$ are as defined above, with the proviso that one of the radicals $R^1$ to $R^5$ on a carbon atom adjacent to a ring nitrogen atom is Z, Z being chlorine, bromine or iodine, and the remaining radicals $R^1$ to $R^5$, if present, are as defined in claim 1, with an aromatic or heteroaromatic hydroxyl compound of the general formula:

R—OH     VI, in which R is an optionally substituted aromatic or heteroaromatic radical.

The following examples illustrate how the process according to the invention is carried out.

EXAMPLE 1

2-Chloro-6-[3-(trifluoromethyl)phenoxy]pyridine 17.45 g (690 mmol) of sodium hydride (95 percent) was suspended in 420 ml of N,N-dimethylacetamide. 106.7 g (658 mmol) of 3 -(trifluoromethyl)phenol was added dropwise over 2 hours at 15° C. The resulting phenate solution was added dropwise over 2.5 hours, under nitrogen, to a solution of 162.4 g (1.097 mol) or 2,6-dichloroyridine in 330 ml of N,N-dimethylacetamide, heated to 90° C. After a further 3 hours of reaction time, the mixture was cooled to room temperature, the sodium chloride which had precipitated out was filtered off and the filtrate was concentrated. The residue was taken up with toluene and 0.1 N hydrochloric acid and the organic phase was washed with saturated sodium chloride solution and concentrated. The oily residue (ca. 200 g) was distilled under vacuum. The yield was 151.5 g (84 percent) of a colorless oil, content (GC): 99.8 percent. Other data concerning the product was:

$n_D^{20}$=1.5267

MS; m/z: 273/275; 238; 39

$^1$H NMR (CDCl$_3$): δ 6.84 (d, J=7.8 Hz, 1H); 7.07 (d, J=7.8 Hz, 1H); 7.35 (m, 1H); 7.42 (m, 1H); 7.45–7.52 (m, 2H); 7.65 (t, J=7.8 Hz, 1H).

$^{13}$C NMR (CDCl$_3$): δ=109.88 (CH); 118.16 (CH); 119.24 (CH); 121.67 (CH); 123.74 (CF$_3$); 124.50 (CH); 130.24 (CH); 132.21 (CCF$_3$); 141.77 (CH); 149.12 (C); 153.89 (C); 162.28 (C).

EXAMPLE 2

3-Chloro-2-[3-(trifluoromethyl)phenoxy]pyridine 7.68 g of sodium hydride dispersion (ca. 50 percent in mineral oil) was washed with pentane under nitrogen and 100 ml of N)N-dimethylformamide was then added. 21.92 g (135 mmol) of 3-(trifluoromethyl)phenol was added dropwise over 30 minutes at room temperature. The resulting phenate solution was added dropwise over 2 hours, under nitrogen, to a solution of 20.1 g (136 mmol) of 2,3-dichloropyridine in 80 ml of N,N-dimethylformamide, heated to 120° C. After 3 hours of reaction time, the mixture was cooled to room temperature, the sodium chloride which had precipitated out was filtered off and the filtrate was concentrated. The residue was extracted with toluene and 0.1 N hydrochloric acid and the organic phase was washed with saturated sodium chloride solution and concentrated. The oily residue was distilled under vacuum. The yield was 24.75 g (67 percent) of a colorless oil, content (GC): 99.7 percent. Other data concerning the product was:

B.p.$_{18mbar}$=145°–148° C.
$n_D^{20}$=1.5282
MS; m/z: 273/275 $^1$H NMR (CDCl$_3$): δ=6.99 (m, 1H); 7.36 (d, 1H); 7.45–7.53 (m, 3H); 7.77 (d, 1H); 8.02 (d, 1H). $^{13}$C NMR (CDCl$_3$): δ118.66 (CH); 119.44 (C); 119.98 (CH); 121.75 (CH); 123.78 (CF$_3$); 124.94 (CH); 130.13 (CH); 132.16 (CCF$_3$); 139.65 (CH); 145.20 (CH); 153.88 (C); 158.51 (C).

EXAMPLE 3

N-(4-Fluorophonyl)-6-[3-(trifluoromethyl)phenoxy]-pyridine-2-carboxamide 10.26 g (37.5 mmol) of 2-chloro-6-[3-(trifluoromethyl)phenoxy]pyridine (content: 99.5 percent, prepared according to Example 1), 6.25 g (56.2 mmol) of 4-fluoroaniline, 4.37 g (41.3 mmol) of sodium carbonate, 26.3 mg (37.5 μmol) of dichlorobis(triphenylphosphine)palladium(II) and 0.40 g (1.125 mmol) of tris(4-methoxyphenyl)phosphine (IV, $R^8=R^9=R^{10}$=methoxy) in 37.5 ml of xylene were placed in an autoclave at room temperature. The autoclave was flushed with inert gas, a carbon monoxide pressure of 5 bar was then applied and the mixture was heated to 150° C. The CO pressure was raised to 18 bar and the mixture was stirred for 21 hours at 150° C. After cooling to room temperature and depressurization, 50 ml of xylene and 50 ml of water were added to the reaction mixture, which was filtered. The aqueous phase was extracted with 25 ml of xylene and the combined organic phases were washed with 30 ml of water. Neither unconverted educt nor by-products were detectable by GC in the xylene phase. After distillation of the solvent, the crude product (15.83 g) was obtained in the form of a yellow solid. The crude product was purified by recrystallization from methylcyclohexane. The yield was 12.13 g (86 percent) of a light beige solid. Other data concerning the product was:

M.p.: 103°–104.5° C.
MS; m/z: 376 (M$^+$), 238
$^1$H NMR (CDCl$_3$): δ=6.99–7.04 (m, 2H); 7.17 (d, J=8.4 Hz, 1H); 7.40 (m, 1H); 7.46–7.51 (m, 2H); 7.55–7.63 (m, 3H); 7.93 (t, J=7.8 Hz, 1H); 8.03 (d, J=7.8 Hz, 1H); 9.24 (br. m, 1H).

EXAMPLE 4

N-(4-Fluorophonyl)-6-[3-(trifluoromethyl)phenoxy]pyridine-2-carboxamide

The procedure was as described in Example 3 except that the dichlorobis(triphenylphosphine)palladium(II) was replaced with the same molar amount of palladium(I) acetate. The CO pressure was 19 bar. This gave 15.77 g of crude product and, after recrystallization, 11.82 g (83.8 percent) of a colorless solid. The M.p. was 104° to 105° C.

EXAMPLE 5

N-(4-Fluorophenyl)-6-[3-(trifluoromethyl)phenoxy]pyridine-2-carboxamide

Analogously to Example 4, 6.84 g (25 mmol) of 2-chloro-6-[3-(trifluoromethyl)phenoxy]pyridine, 3.33 g (30 mmol) of 4-fluoroaniline, 2.92 g (27.5 mmol) of sodium carbonate, 5.6 mg (25 μmol) of palladium(II) acetate and 260 mg (0.75 mmol) of tris(4-methoxyphenyl)phosphine in 25 ml of methylcyclohexane were reacted under a CO pressure of 7.5 bar for 20 hours. After cooling to 80° C., the reaction mixture was diluted with 65 ml of warm methylcyclohexane. The salts were filtered off and washed with 10 ml of warm methylcyclohexane. On cooling to 5° C. the product crystallized. The yield was 8.1 g (86 percent) of a light beige solid. The melting point was 104.5° to 105.1° C.

EXAMPLE 6

N-(4-Fluorophonyl)-6-[3-(trifluoromethyl)phanoxy]pyridine-2-carboxamide

The procedure was as described in Example 3 except that the tris(4-methoxyphenyl)phosphine was replaced with the same molar amount of tris(4-methylphenyl)phosphine (IV, $R^8=R^9=R^{10}$=methyl). The CO pressure was 20 bar and the reaction time was 21 hours. The composition of the dissolved products in the xylene phase was determined by GC. 94.1 percent of the title compound and 5.9 percent of educt were found.

EXAMPLE 7

N-(4-Fluorophonyl)-6-[3-(trifluoromethyl)phenoxy]pyridine-2-carboxamide

The procedure was as described in Example 3 except that the tris(4-methoxyphenyl)phosphine was replaced with the same molar amount of tris(4-fluorophenyl)phosphine (IV, $R^8=R^9=R^{10}$=fluorine). The CO pressure was 19 bar and the reaction time was 21 hours. The composition of the dissolved products in the xylene phase was determined by GC. 90.8 percent of the title compound and 9.2 percent of educt were found.

EXAMPLE 8

N-(4-Fluorophenyl)-6-[3-(trifluoromethyl)phenoxy]pyridine-2-carboxamide

The procedure was as described in Example 4 except that the tris(4-methoxyphenyl)phosphine was replaced with the same molar amount of tris(4-benzyloxyphenyl)phosphine (IV, $R^8=R^9=R^{10}$=benzyloxy). The composition of the dissolved products in the xylene phase was determined by GC. 99.1 percent of the title compound, 0.5 percent of educt and 0.2 percent of N-(4-fluorophenyl)-6-[3-(trifluoromethyl)phenoxy]pyridine-2-amine were found.

EXAMPLES 9 TO 12

N-(4-Fluorophenyl)-6-[3-(trifluoromethyl)phonoxy]pyridine-2-carboxamide

The procedure was as described in Example 4 except that the reaction time was shortened to 6 hours and various solvents were employed. The composition of the dissolved products in the organic phase was determined by GC. The results are compiled in the following Table I.

TABLE I

| Solvent | Product [%] | Educt [%] | 4-Fluoroaniline [%] |
| --- | --- | --- | --- |
| Methylcyclohexane | 87.3 | 7.2 | 5.2 |
| Pyridine | 79.5 | 7.7 | 12.8 |
| N,N-Dimethylacetamide | 74.4 | 15.0 | 10.6 |
| Butyl acetate | 72.6 | 19.8 | 7.3 |

EXAMPLE 13

2-Chloro-6-[1-methyl-3-(trifluoromethyl)pyrazol-5-yloxy]pyridine 1.8 g (71 mmol) of sodium hydride (95 percent) was suspended in 25 ml of N,N-dimethylacetamide. A solution of 12.46 g (67 mmol) of 1-methyl-5-hydroxy-3-(trifluoromethyl)pyrazole (*J. Heterocycl. Chem.* 1990, 27, 243) in 40 ml of N,N-dimethylacetamide was added dropwise over 1 hour at 22° C. The resulting solution was added dropwise over 3 hours, under nitrogen, to a solution of 18.5 g (125 mmol) of 2,6-dichloropyridine in 37.5 ml of N,N-dimethylacetamide, heated to 135° C. After a further 5 hours of reaction time, the mixture was cooled to room temperature, the sodium chloride which had precipitated out was filtered off and the filtrate was concentrated. The residue was taken up with toluene and water and the organic phase was washed with saturated sodium chloride solution and concentrated. The solid residue was distilled under vacuum. The title compound distills at 175° C. under 25 mbar. This gave 12.5 g of crude product in the form of a yellow solid (96 percent pure, GC). This was purified by recrystallization from diisopropyl ether. The yield was 11:55 g (62 percent) of colorless crystals, content (GC): 99.9 percent. Other data concerning the product was:

M.p.: 56°–58° C.

MS; m/z: 277/279

$^1$H NMR (CDCl$_3$): δ=3.80 (s, 3H); 6.40 (s, 1H); 6.96 (d, J=8.2 Hz, 1H); 7.18 (d, J=8.2 Hz, 1H); 7.74 (t, J=8.2 Hz, 1H).

EXAMPLE 14

N-(4-Fluorophenyl)-6-[1-methyl-3-(trifluoromethyl) pyrazol-5-yloxy]pyridine-2-carboxamide The procedure was as described in Example 4. 4.92 g of crude product was obtained in the form of a light yellow solid from 3.47 g (12.5 mmol) of 2-chloro-6-[1-methyl-3-(trifluoromethyl)pyrazol-5-yloxy]pyridine, 2.08 g (18.7 mmol) of 4-fluoroaniline, 1.46 g (13.8 mmol) of sodium carbonate, 5.6 mg (25 μmol) of palladium(II) acetate and 0.13 g (375 μmol) of tris(4-methoxyphenyl)phosphine in 12.5 ml of xylene after 21 hours at 150° C. under a CO pressure of 19 bar (GC: complete conversion). It was purified by recrystallization from methylcyclohexane. The yield was 3.97 g (84.4 percent) of light beige crystals. Other data concerning the product was:

M.p.: 138°–139° C.

$^1$H NMR (CDCl$_3$): δ=3.85 (s, 3H); 6.41 (s, 1H); 7.06 (m, 2H); 7.29 (d, J=8.1 Hz, 1H); 7.59 (m, 2H); 8.05 (t, J=8.1 Hz, 1H); 8.14 (d, J=8.1 Hz, 1H); 9.28 (bs, 1H).

EXAMPLE 15

N-Phanyl-6-[3-(trifluoromethyl)phenoxy]pyridine-2-carboxamide

The procedure was as described in Example 5 except that the 4-fluoroaniline was replaced with 2.79 g (30 mmol) of aniline and the amount of palladium(II) acetate was doubled (50 μmol). The CO pressure was 19 bar. The yield was 72.8 percent of a beige solid. The melting point was 92° to 93° C. (from methylcyclohexane). Other data concerning the product was:

MS; m/z: 358 (M$^+$), 239; 238; 39 (100 percent)

$^1$H NMR (CDCl$_3$): δ=7.11 (t, J=7.3 Hz, 1H); 7.18 (d, J=8.1 Hz, 1H); 7.33.(tJ=7.3 Hz, 2H);7.41 (m, 1H); 7.52 (m, 2H); 7.55 (m, 1H); 7.59 (m, 2H); 7.95 (dd, J=7.3/0.8 Hz, 1H); 8.04 (d, J=7.3 Hz, 1H) 9.27 (br. s, 1H).

EXAMPLE 16

N-(3-Fluorophenyl)-6-[3-(trifluoromethyl)phenoxy] pyridine-2-carboxamide

The procedure was as described in Example 15 except that the aniline was replaced with 3.33 g (30 mmol) of 3-fluoroaniline. The CO pressure was 20 bar. The yield was 73 percent of a beige solid. The melting point was 74° to 75° C. (from methylcyclohexane). Other data concerning the product was:

MS; m/z: 376 (M$^+$); 238; 39 (100 percent)

$^1$H NMR (CDCl$_3$): δ=6.80 (m, 1H); 7.05 (d, j=7 Hz, 1H); 7.19 (d, J=8.1 Hz, 1H); 7.25 (m, 1H); 7.41 (m, 1H); 7.54 (m, 2H); 7.60 (m, 2H); 7.96 (dd, J=7.3/0.8 Hz, 1H); 8.03 (d, J=7.3 Hz, 1H); 9.31 (br. s, 1H).

EXAMPLE 17

N-(2,4-Difluorophenyl)-6-[3-(trifluoromethyl)phenoxy] pyridine-2-carboxamide

The procedure was as described in Example 15 except that the aniline was replaced with 3.87 g (30 mmol) of 2,4-difluoroaniline. The CO pressure was 20 bar. The yield was 80.5 percent of a beige solid. The melting point was 110.5° to 111.5° C. (from methylcyclohexane). Other data concerning the product was:

MS; m/z: 394 (M$^+$); 238; 39 (100 percent)

$^1$H NMR (CDCl$_3$): δ=6.85 (m, 2H); 7.23 (m, 1H); 7.45 (m, 2H); 7.58 (m, 2H); 7.99 (m, 2H); 8.45 (m, 1H); 9.48 (br. s, 1H).

EXAMPLE 18

N-[3-(Trifluoromethyl)phenyl]-6-[3-(trifluoromethyl) phenoxy]pyridine-2-carboxamide The procedure was as described in Example 15 except that the aniline was replaced with 5.09 g (30 mmol, 95 percent content) of 3-(trifluoromethyl)aniline and 1.2 mmol of tris(4-methoxyphenyl)phosphine was employed. The CO pressure was 20 bar. The yield was 75.4 percent of a beige solid. The melting point was 93.10 to 93.7° C. (from methylcyclohexane). Other data concerning the product was:

MS; m/z: 426 (M$^+$); 238; 39 (100 percent)

$^1$H NMR (CDCl$_3$): δ=7.21 (d, J=8.1 Hz, 1H); 7.37 (m, 1H); 7.43 (m, 2H); 7.57 (m, 1H); 7.62 (m, 2H); 7.69 (d, J=8.1 Hz, 1H); 7.82 (s, 1H); 7.96 (dd, J=7.3/0.6 Hz, 1H); 8.04 (d, J=7.3 Hz, 1H); 9.39 (br. s, 1H).

EXAMPLE 19

N-[4-(Trifluoromethyl)phanyl]-6-[3-(trifluoromethyl) phenoxy]pyridine-2-carboxamide The procedure was as described in Example 18 except that the 3-(trifluoromethyl)aniline was replaced with 4.93 g (30 mmol, 98 percent content) of 4-(trifluoromethyl)aniline. The CO pressure was 20 bar. The yield was 79.6 percent of a beige solid. The melting point was 130.5° to 132° C. (from methylcyclohexane). Other data concerning the product was:

MS; m/z: 426 (M$^+$); 238; 39 (100 percent) $^1$H NMR (CDCl$_3$): δ=7.21 (d, J=8.1 Hz, 1H); 7.42 (m, 1H); 7.60 (m, 7H); 7.97 (t, J=7.3 Hz, 1H); 8.05 (d, J=7.3 Hz, 1H); 9.41 (br. s, 1H).

EXAMPLE 20

N-(2,2,2-Trifluoroethyl)-6-[1-methyl-3-(trifluoromethyl) pyrazol-5-yloxy]pyridine-2-carboxamide Analogously to Example 14, 1.39 g (5 mmol) of 2-chloro-6-[1-methyl-3-(trifluoromethyl)-pyrazol-5-yloxy]pyridine, 0.75 g (7.57 mmol, 98 percent content) of 2,2,2-trifluoroethylamine, 0.80 g (7.55 mmol) of anhydrous sodium carbonate, 5.6 mg (25 μmol) of palladium(II) acetate and 88 mg (0.25 mmol) of tris(4-methoxyphenyl)phosphine in 20 ml of methylcyclohexane were reacted under a CO pressure of 21 bar. The yield was 0.96 g (75.4 percent) of a white solid. The melting point was 135.8° to 136.3° C. (from methylcyclohexane). Other data concerning the product was:

MS; m/z: 368 (M$^+$); 242 (100 percent) $^1$H NMR (CDCl$_3$): δ=3.82 (s, 3H); 4.05 (m, 2H); 6.29 (s, 1H); 7.27 (dt, J=8.1/0.6 Hz, 1H); 7.64 (br. s, 1H); 8.01 (dd, J=7.3/0.5 Hz, 1H); 8.07 (d, J=7.3 Hz, 1H).

COMPARATIVE EXAMPLE 1

The procedure was analogous to Example 3 except that the tris(4-methoxyphenyl)phosphine was replaced with the same molar amount of triphenylphosphine. After a reaction time of 15.5 hours at a CO pressure of 15 bar, the composition of the dissolved products in the xylene phase was determined by GC. Only 43.2 percent of the desired product and 56.8 percent of unconverted educt were found.

COMPARATIVE EXAMPLE 2

The procedure was as described in Example 3 except that the tris(4-methoxyphenyl)phosphine was replaced with the same molar amount of tri-n-butylphosphine. After a reaction time of 15 hours at a CO pressure of 14 bar, the composition of the dissolved products in the xylene phase was determined by GC. Only traces (0.4 percent) of the desired product and 96.8 percent of unconverted educt were found.

COMPARATIVE EXAMPLE 3

The procedure was as described in Example 3 except that the tris(4-methoxyphenyl)phosphine was replaced with the same molar amount of tris(3-methoxyphenyl)phosphine. After a reaction time of 21 hours at a CO pressure of 19 bar, the composition of the dissolved products in the xylene phase was determined by GC. Only 53.3 percent of the desired product and 46.7 percent of unconverted educt were found.

COMPARATIVE EXAMPLE 4

The procedure was analogous to Example 3 except that the tris(4-methoxyphenyl)phosphine was replaced with the same molar amount of tris(2-methoxyphenyl)phosphine. After a reaction time of 21 hours at a CO pressure of 19 bar, the composition of the xylene phase was determined by GC. Only unconverted educt was found, with no products at all being found.

COMPARATIVE EXAMPLE 5

The procedure was analogous to Example 3 except that the tris(4-methoxyphenyl)phosphine was replaced with the same molar amount of tris(4-chlorophenyl)phosphine. After a reaction time of 21 hours at a CO pressure of 20 bar, the composition of the dissolved products in the xylene phase was determined by GC. Only 26.3 percent of the desired product and 73.7 percent of unconverted educt were found.

What is claimed is:

1. A process for the preparation of an amide of the formula:

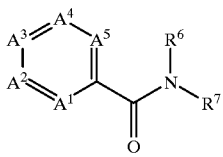

I wherein:
$A^1$ is nitrogen or $CR^1$,
$A^2$ is nitrogen or $CR^2$,
$A^3$ is nitrogen or $CR^3$,
$A^4$ is nitrogen or $CR^4$ and
$A^5$ is nitrogen or $CR^5$,
with the proviso that at least one of the ring members $A^1$ to $A^5$ is nitrogen and that two nitrogen atoms are not bonded directly to one another;
$R^1$ to $R^5$, if present, independently of one another are hydrogen, $C_{1-4}$-alkyl or aryl, but one of the substituents $R^1$ to $R^5$ is a group of the formula —OR, wherein R is an optionally substituted aromatic or heteroaromatic radical, said optional substituents being ones which will not undergo alkylation;
$R^6$ is hydrogen or $C_{1-4}$-alkyl; and
$R^7$ is an optionally substituted aromatic or heteroaromatic radical, comprising reacting a halogen compound of the formula:

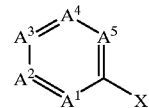

II wherein $A^1$ to $A^5$ are as defined above and X is chlorine, bromine, or iodine, directly with carbon monoxide and a primary or secondary amine of the formula:

III wherein $R^6$ and $R^7$ are as defined above, in the presence of a complex of palladium with a triphenylphosphine of the formula:

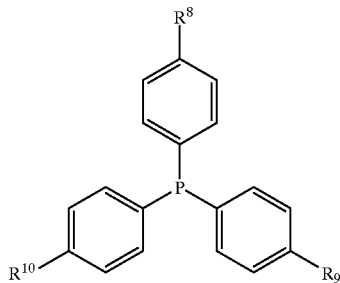

IV wherein $R^8$ to $R^{10}$ independently of one another are $C_{1-4}$-alkyl, or fluorine, and with a base other than a primary or secondary or tertiary amine.

2. The process according to claim 1, wherein $A^2$ is nitrogen and part of a pyridine ring.

3. The process according to claim 2, wherein $R^1$ is a group of the formula —OR, R being an optionally substituted aromatic or heteroaromatic radical.

4. The process according to claim 3, wherein R is an optionally substituted phenyl group.

5. The process according to claim 1, wherein $A^1$ is nitrogen and part of a pyridine ring.

6. The process according to claim 5, wherein $R^2$ is a group of the formula —OR, R being an optionally substituted aromatic or heteroaromatic radical.

7. The process according to claim 1, wherein $A^1$ and $A^5$ are nitrogen and part of a pyrimidine ring.

8. The process according to claim 7, wherein $R^2$ is a group of the formula —OR, R being an optionally substituted aromatic or heteroaromatic radical.

9. The process according to claim 1, wherein $A^1$ and $A^4$ are nitrogen and part of a pyrazine ring.

10. The process according to claim 9, wherein $R^2$ is a group of the formula —OR, R being an optionally substituted aromatic or heteroaromatic radical.

11. The process according to claim 1, wherein $A^1$, $A^3$ and $A^5$ are nitrogen.

12. The process according to claim 11, wherein $R^2$ is a group of the formula —OR, R being an optionally substituted aromatic or heteroaromatic radical.

13. The process according to claim 12, wherein R is an optionally substituted phenyl group.

14. The process according to claim 12, wherein $R^6$ is hydrogen and $R^7$ is an optionally substituted phenyl group.

15. The process according to claim 14, wherein X is chlorine.

16. The process according to claim 1, wherein $R^6$ is hydrogen and $R^7$ is an optionally substituted phenyl group.

17. The process according to claim 1, wherein X is chlorine.

18. The process according to claim 15, wherein $R^8$ to $R^{10}$ are identical and are $C_{1-4}$-alkyl groups.

19. The process according to claim 15 wherein $R^8$ to $R^{10}$ are fluorine.

20. The process according to claim 1, wherein $R^8$ to $R^{10}$ are identical and are $C_{1-4}$-alkyl groups.

21. The process according to claim 1, wherein $R^8$ to $R^{10}$ are fluorine.

22. A process for the preparation of an amide of the formula:

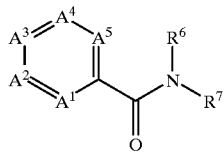

I wherein:

- $A^1$ is nitrogen or $CR^1$,
- $A^2$ is nitrogen or $CR^2$,
- $A^3$ is nitrogen or $CR^3$,
- $A^4$ is nitrogen or $CR^4$ and
- $A^5$ is nitrogen or $CR^5$,
- with the proviso that at least one of the ring members $A^1$ to $A^5$ is nitrogen and that two nitrogen atoms are not bonded directly to one another;
- $R^1$ to $R^5$, if present, independently of one another are hydrogen, $C_{1-4}$-alkyl or aryl, but one of the substituents $R^1$ to $R^5$ is a group of the formula —OR, wherein R is an optionally substituted aromatic or heteroaromatic radical;
- $R^6$ is hydrogen or $C_{1-4}$-alkyl; and
- $R^7$ is an optionally substituted aromatic or heteroaromatic radical, said optional substituents being ones which will not undergo alkylation, comprising, in a first step, reacting a dihalide of the general formula:

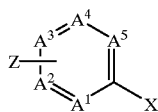

V wherein $A^1$ to $A^5$ are as defined above, X is chlorine, bromine, or iodine, one of the radicals $R^1$ to $R^5$ on a carbon atom adjacent to a ring nitrogen atom is Z, Z being chlorine, bromine, or iodine, and the remaining radicals $R^1$ to $R^5$, if present, are as defined above, with an aromatic or heteroaromatic hydroxyl compound of the formula:

 VI wherein R is as defined above, to give a (hetero)aryloxy halogen compound of the formula:

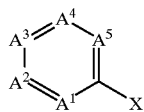

II wherein $A^1$ to $A^5$ are as defined above, and, in a second step, reacting said product of formula II with carbon monoxide and a primary or secondary amine of the formula:

 III wherein $R^6$ and $R^7$ are as defined above, in the presence of a complex of palladium with a triphenylphosphine of the formula:

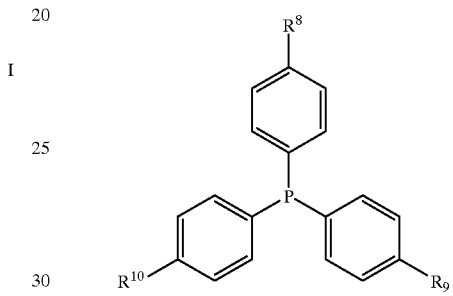

IV wherein $R^8$ to $R^{10}$ independently of one another are $C_{1-4}$-alkyl, or fluorine, and with a base other than a primary or secondary or tertiary amine.

23. A process for the preparation of an amide of the formula

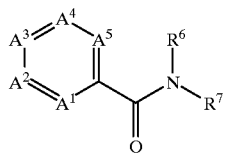

wherein:

- $A^1$ is nitrogen or $CR^1$,
- $A^2$ is nitrogen or $CR^2$,
- $A^3$ is nitrogen or $CR^3$,
- $A^4$ is nitrogen or $CR^4$ and
- $A^5$ is nitrogen or $CR^5$,
- with the proviso that at least one of the ring members $A^1$ to $A^5$ is nitrogen and that two nitrogen atoms are not bonded directly to one another;
- $R^1$ to $R^5$, if present, independently of one another are hydrogen, $C_{1-4}$-alkyl or aryl, but one of the substituents $R^1$ to $R^5$ is a group of the formula —OR, wherein R is an optionally substituted aromatic or heteroaromatic radical;
- $R^6$ is hydrogen or $C_{1-4}$-alkyl; and
- $R^7$ is an optionally substituted aromatic or heteroaromatic radical, said optional substituents being ones which will not undergo alkylation, comprising reacting a halogen compound of the formula:

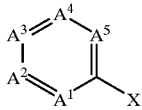

II wherein $A^1$ to $A^5$ are as defined above and X is chlorine, bromine, or iodine, directly with carbon monoxide and a primary or secondary amine of the formula:

$R^6$—NH—$R^7$   III wherein $R^6$ and $R^7$ are as defined above, in the presence of a complex of palladium with a triphenylphosphine of the formula:

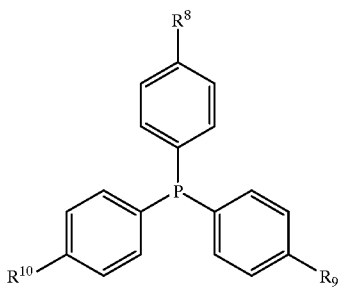

IV wherein $R^8$ to $R^{10}$ independently of one another are $C_{1-4}$-alkyl, $C_{1-4}$-alkoxy, fluoro, or benzyloxy, provided at least one of $R^8$, $R^9$, and $R^{10}$ is benzyloxy, and with a base other than k primary or secondary or tertiary amine.

24. The process of claim 23 wherein $R^8$ to $R^{10}$ are each benzyloxy.

25. A process for the preparation of an amide of the formula:

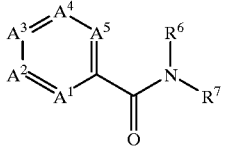

I wherein:
$A^1$ is nitrogen or $CR^1$,
$A^2$ is nitrogen or $CR^2$,
$A^3$ is nitrogen or $CR^3$,
$A^4$ is nitrogen or $CR^4$ and
$A^5$ is nitrogen or $CR^5$,
with the proviso that at least one of the ring members $A^1$ to $A^5$ is nitrogen and that two nitrogen atoms are not bonded directly to one another;
$R^1$ to $R^5$, if present, independently of one another are hydrogen, $C_{1-4}$-alkyl or aryl, but one of the substituents $R^1$ to $R^5$ is a group of the formula —OR, wherein R is an optionally substituted aromatic or heteroaromatic radical;
$R^6$ is hydrogen or $C_{1-4}$-alkyl; and
$R^7$ is an optionally substituted aromatic or heteroaromatic radical, said optional substituents being ones which will not undergo alkylation, comprising, in a first step, reacting a dihalide of the general formula:

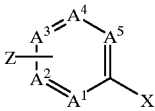

V wherein $A^1$ to $A^5$ are as defined above, X is chlorine, bromine, or iodine, one of the radicals $R^1$ to $R^5$ on a carbon atom adjacent to a ring nitrogen atom is Z, Z being chlorine, bromine, or iodine, and the remaining radicals $R^1$ to $R^5$, if present, are as defined above, with an aromatic or heteroaromatic hydroxyl compound of the formula:

R—OH   VI where R is as defined above, to give a (hetero)aryloxy halogen compound of the formula:

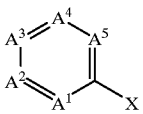

II wherein $A^1$ to $A^5$, R and X are as defined above, and, in a second step reacting said product of formula II with carbon monoxide and a primary or secondary amine of the formula:

$R^6$—NH—$R^7$   III wherein $R^6$ and $R^7$ are as defined above, in the presence of a complex of palladium with a triphenylphosphine of the formula:

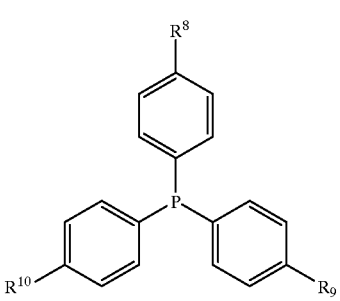

IV wherein $R^8$ to $R^{10}$ independently of one another are $C_{1-4}$-alkyl, $C_{1-4}$-alkoxy, fluoro, or benzyloxy, provided at least one of $R^8$, $R^9$, and $R^{10}$ is benzyloxy, and with a base other than said primary or secondary or tertiary amine. —

26. The process of claim 25 wherein $R^8$ to $R^{10}$ are each benzyloxy.

27. The process of claim 1 wherein the base is a carbonate, an acetate, a phosphate, or a hydrogen phosphate.

* * * * *